US00PP15582P3

(12) United States Plant Patent
Casertano

(10) Patent No.: US PP15,582 P3
(45) Date of Patent: Feb. 22, 2005

(54) ***SEDUM* PLANT NAMED 'SAMUEL OLIPHANT'**

(50) Latin Name: *Sedum spectabile*
Varietal Denomination: Samuel Oliphant

(75) Inventor: John L. Casertano, 1308 S. Meriden Rd., Cheshire, CT (US) 06410

(73) Assignee: John L. Casertano, Cheshire, CT (US)

( * ) Notice: Subject to any disclaimer, the term of this patent is extended or adjusted under 35 U.S.C. 154(b) by 80 days.

(21) Appl. No.: 10/681,958

(22) Filed: Oct. 10, 2003

(65) Prior Publication Data

US 2005/0010985 P1 Jan. 13, 2005

(30) Foreign Application Priority Data

Jul. 11, 2003 (EP) ..... 2003/1307

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—S B McCormick-Ewoldt

(57) ABSTRACT

*Sedum* 'Samuel Oliphant' is a new and distinct cultivar of Stonecrop plant having gray-green leaves with creamy-yellow margins and carmine tips, and long lasting pinkish flowers valuable as a landscaping specimen, potted plant, or cut flower.

3 Drawing Sheets

BACKGROUND OF THE INVENTION

The present invention relates to the new and distinct cultivar of Stonecrop, botanically known as *Sedum spectabile* 'Samuel Oliphant', and hereinafter referred to as the cultivar 'Samuel Oliphant' or the "Plant". The new Plant was discovered and developed by the inventor, John Louis Casertano, in 2000, as a non-induced sport of *Sedum* 'Matrona' (not patented), at a nursery in Cheshire, Conn., USA. Mr. Casertano has propagated the plant by division and stem cuttings at the same nursery, and found that the subsequent plants are identical to the original selection.

BRIEF SUMMARY OF THE PLANT

*Sedum* 'Samuel Oliphant' is unique from all other sedums. Other variegated forms of *Sedum spectabile* exist, *Sedum* 'Pink Chablis' PPAF, *Sedum* 'Lajos' U.S. Plant Pat. No. 14,421, *Sedum* 'Frosty Morn' (not patented) and *Sedum* 'Mediovariegata' (not patented) or *Sedum* 'Variegata' (not patented), but no other form has the same creamy yellow margin with burgundy tinting to the stem and leaf tips. The Plant has not been observed in all possible environments. The phenotype may vary slightly with variations in growing conditions such as light intensity and day length, temperature, water availability, and nutrient availability, without, however any variance in genotype.

The Plant is slightly smaller than *Sedum* 'Matrona' in stature, but nearly identical to it in all other characteristics, including flower, with the simple exception of the light creamy-yellow variegated leaf margin.

The following are traits of *Sedum* 'Samuel Oliphant':

1. Attractive deep gray-green leaves with creamy-yellow margins and carmine tips.
2. Carmine buds lightening to a cream bud with carmine tinting before opening.
3. Pinkish flower.
4. Magenta stems.

BRIEF DESCRIPTIONS OF THE DRAWINGS

The photographs of the new plant demonstrate the unique characteristics and overall appearance of the new cultivar 'Samuel Oliphant'. The colors are as accurate as reasonably possible with color reproductions. Variations in light source, quality and direction may cause the appearance of different colors.

Figure 1:
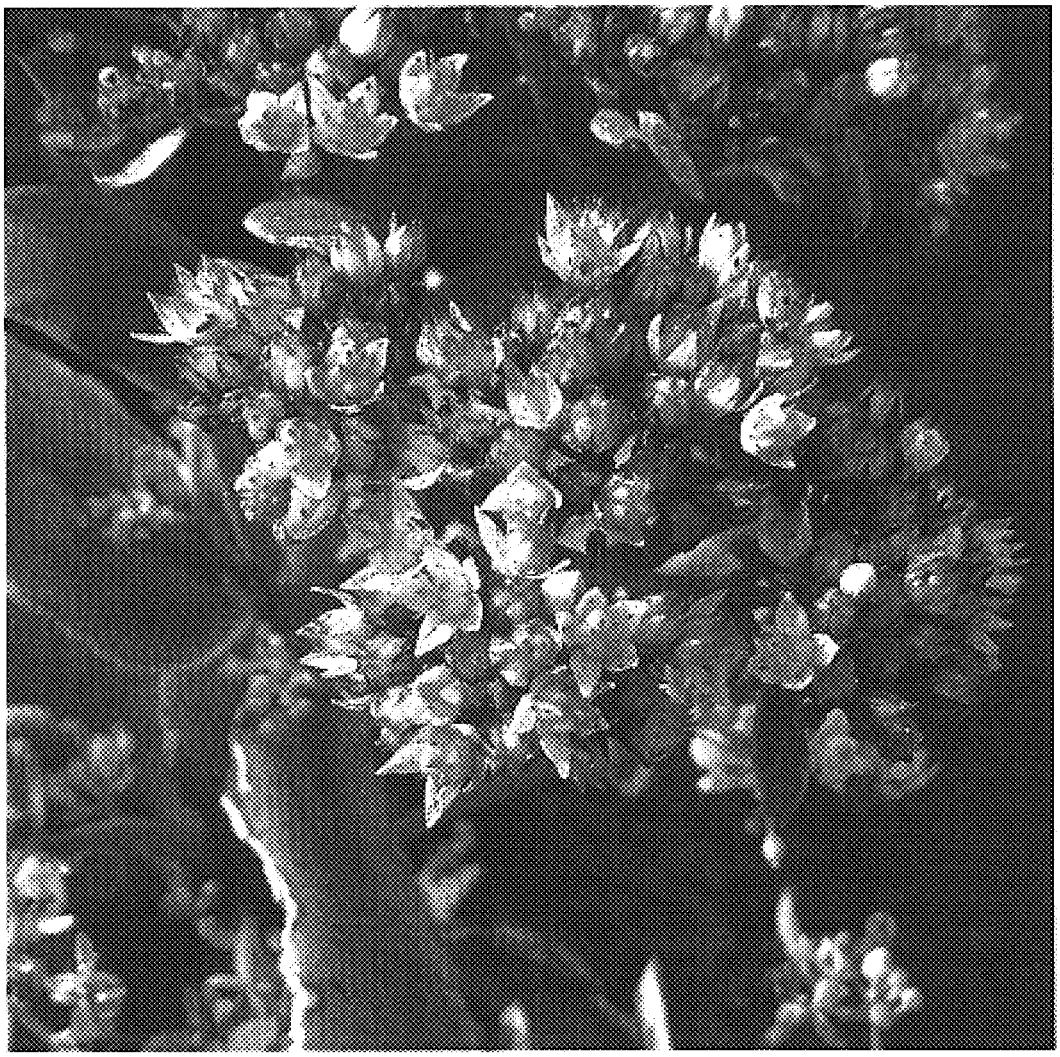

FIG. 1—Shows the plant in flower.

Figure 2:
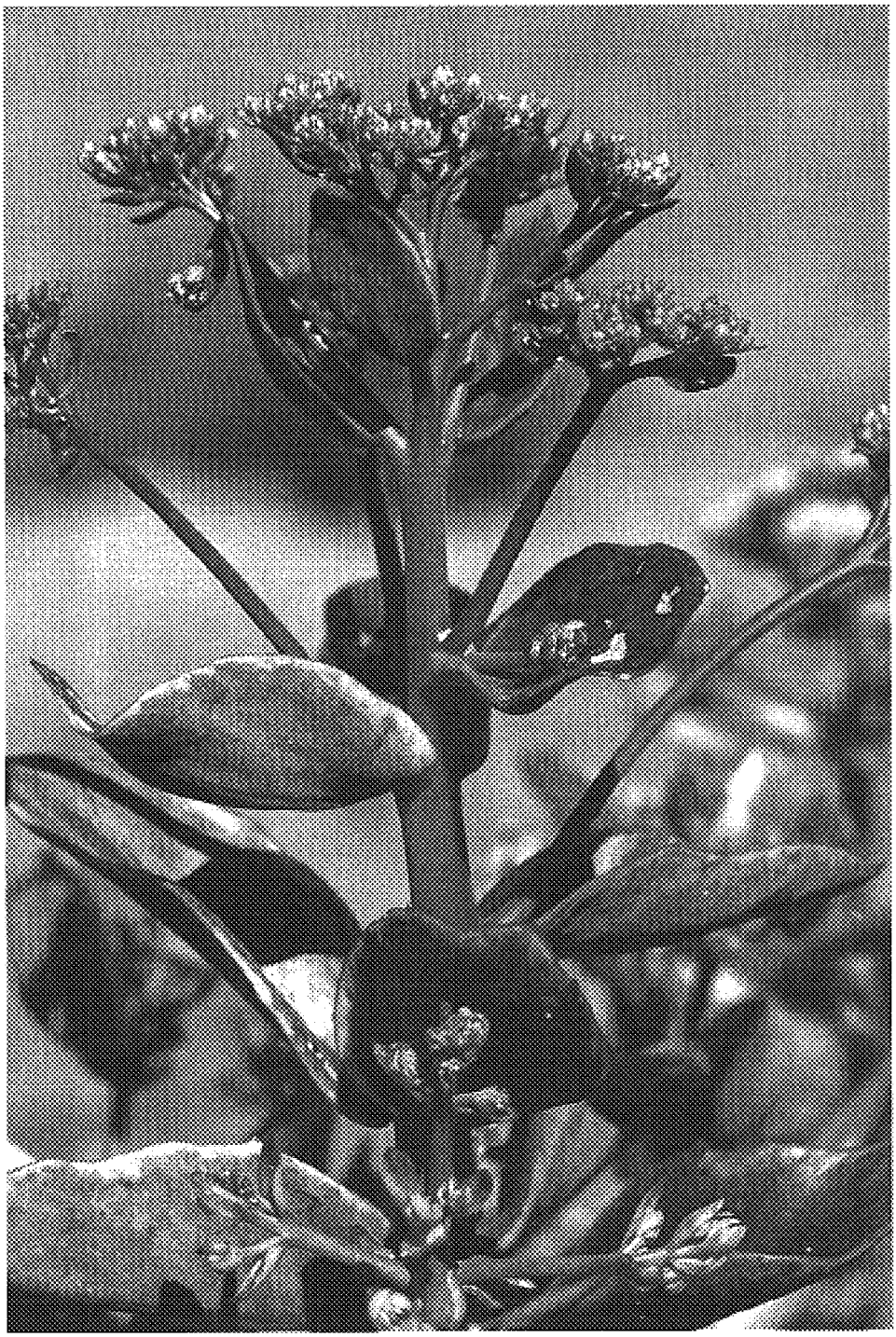

FIG. 2—Shows the plant while in early bud.

Figure 3:
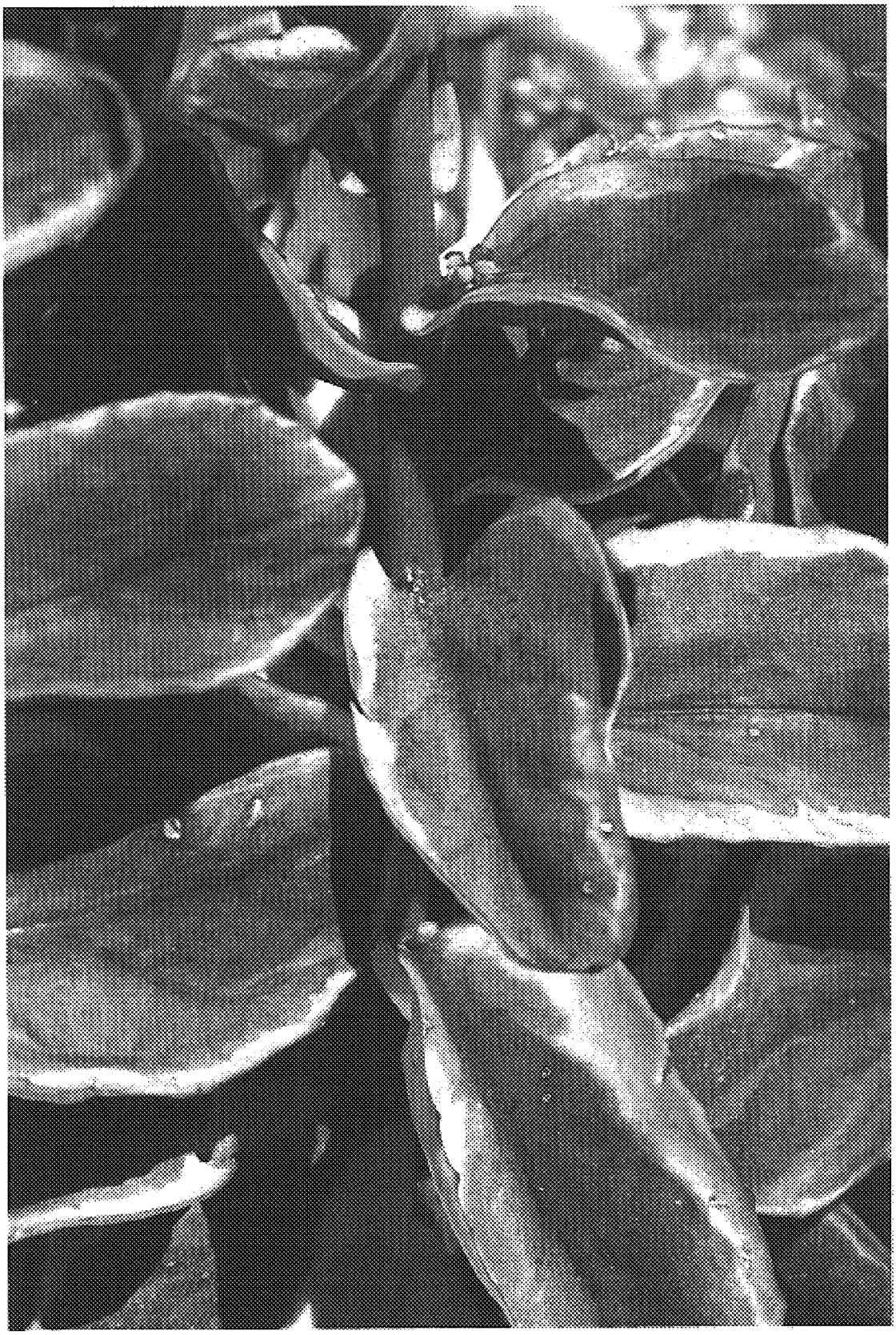

FIG. 3—Shows a close-up of the variegated leaves.

DETAILED BOTANICAL DESCRIPTION

The following description uses color references according to the 2001 edition of "The Royal Horticultural Society Colour Chart", except where general dictionary terms are used. The plant has been observed in outdoor trial gardens in Zeeland, Mich., Cheshire, Conn. and greenhouses in both locations. The Plant in both trial gardens performed the same, while the Plant grown in a greenhouse environment showed less carmine tinting to the foliage. The plant described is two-years old from cuttings, grown in a well-drained, loamy sand soil, full-sun trail gardens of a nursery in Zeeland, Mich., United States of America, with supplemental fertilization and irrigation.

Botanical classification: Family — Crassulaceae; *Sedum spectabile* (Boreau) hybrid 'Samuel Oliphant'.

Parentage: *Sedum* 'Matrona' (not patented) sport.

Propagation: Asexual by cutting, division or by tissue culture.

Rooting time: Approximately two to three weeks.

Root description: Tuberous, coarse.

Plant habit and form: Erect stems 1.5 to 2.0 cm in diameter, producing plants between 45 cm and 60 cm tall, 45 cm to 55 cm wide, with alternate leaves. Internode length varies depending on age of plant and openness of crown with young, more open plants being nearly whorled to internodes of up to 2 cm.

Growth rate: Medium, developing several stems in a 20 cm pot in 12 weeks from cuttings.

Leaves: Oblong, slightly conduplicate, obtuse tip; without petioles; to 15 cm long by 8 cm wide, decreasing in size on the stem with last leaves before the panicle about 5.5 cm long 2.5 cm wide; denticulate; reticulate veined; center portion adaxial side RHS N138 C, abaxial side RHS 190 A; margin RHS 18 B adaxial and abaxial; edge RHS 53 C, with some tinting of RHS 53 C on the top surface near the stem.

Buds: Carmine, RHS 60 A, effective in mid-July; buds developing to pinkish RHS 55 C with deeper carmine tips in early August.

Umbel: 20 to 25 cm across, heavily branched.

Peduncle: Up to 12 cm long and 5 mm in diameter; about RHS 183 C with a glaucous bloom.

Pedicel: 3 to 5 mm long, about one mm in diameter; RHS 65 C.

Bud: Globose, 3 mm wide, 4 mm long; nearest RHS 36 D two days before opening.

Flowers: Starting in late August and lasting for four weeks through September, approximately 1000 to 1200 per stem.

Petals: Five, rarely four; 5 mm long, 3 mm wide, RHS 65 D both sides.

Sepals: None observed.

Style: Five, rarely four; 4 mm long, swollen in center to nearly 2 mm, proximal end RHS 65 C, distal RHS 64 C.

Androecium: Ten stamens, filaments 2 to 3 mm long, less than one mm diameter, RHS 65 D; anthers less than one mm, darker than RHS N187 A.

Pollen: None observed.

Fruit: None observed.

Fragrance: None detected.

The Plant performs best with fertilization in soils with good drainage but is resistant to drought and heat, as well as cold tolerant to at least USDA Zone 3.

I claim:

1. I claim the new and distinct variety of Stonecrop plant, *Sedum spectabile* 'Samuel Oliphant', essentially as herein described and illustrated, having gray-green leaves with creamy-yellow margins and carmine tips, and long lasting pinkish flowers valuable as a landscaping specimen, plotted plant, or cut flower.

* * * * *